United States Patent [19]
Lahoda et al.

[11] Patent Number: 5,443,732
[45] Date of Patent: Aug. 22, 1995

[54] BORON ISOTOPE SEPARATION USING CONTINUOUS ION EXCHANGE CHROMATOGRAPHY

[75] Inventors: Edward J. Lahoda, Pittsburgh; C. Y. Lin, Monroeville; J. A. Battaglia, Forest Hills; A. J. Impink, Jr., Murrysville, all of Pa.

[73] Assignee: Westinghouse Electric Corporation, Pittsburgh, Pa.

[21] Appl. No.: 222,427

[22] Filed: Apr. 1, 1994

[51] Int. Cl.6 .............................................. B01D 15/08
[52] U.S. Cl. .................................. 210/635; 210/656; 210/657; 210/659; 210/198.2; 423/100; 423/112; 423/283; 423/DIG. 7
[58] Field of Search ............... 423/100, 112, 283, 298, 423/592, 622, DIG. 7; 210/635, 656, 657, 659, 198.2

[56] References Cited

U.S. PATENT DOCUMENTS

| | | | |
|---|---|---|---|
| 4,915,843 | 4/1990 | Taniguchi | 210/659 |
| 5,024,749 | 6/1991 | Snyder | 210/198.2 |
| 5,045,209 | 9/1991 | Snyder | 210/656 |
| 5,098,678 | 3/1992 | Lee et al. | 423/70 |
| 5,110,566 | 5/1992 | Snyder | 423/DIG. 7 |
| 5,112,493 | 5/1992 | Snyder et al. | 210/656 |
| 5,124,023 | 6/1992 | Bosserman | 210/659 |
| 5,133,869 | 7/1992 | Taniguchi | 210/659 |
| 5,174,971 | 12/1992 | Snyder | 423/DIG. 7 |
| 5,176,885 | 1/1993 | Impink, Jr. et al. | 423/6 |

OTHER PUBLICATIONS

H. Kakihana, et al., Equilibrium Constants For Boron Isotope-Exchange Reactions, Bull. Res. Lab. Nuclear Reactors, vol. 2, pp. 1-12 (1977).
H. Kakihana, Estimation of Isotope Separation Power of Chromatography, Separation Sci and Tech., vol. 15, No. 3, pp. 567-585 (1980).
Y. Sakuma, et al., Boron Isotope Separation By Ion Exchange Chromatography Using Weakly Basic Anion Exchange Resin, Bull. Chem. Soc. Jpn., vol. 53, No. 7, pp. 1860-1863 (1980).
R. S. de Miera, et al., Separation De Los Isotopes Estables Del Boro for Cromatografia De Intercambio Ionico 1.—Determinacion de factores de factores de separacion, Junta De Energia Nuclear NTIS 75643, JEN 580 (1985) pp. 1-67.
M. Perie, Analyse Et Separation Des Isotopes Du Bore, Commissariat A L'Energie Atomique, CEA-R 3230 (1967) pp. 1-69.
M. Kotaka, et al., Separation of Boron Isotopes By Means of Weak-Base Anion Exchange Resin, Jpn. Chem. Soc., vol. 8, p. 1482 (1973).
P. Cohen, Water Coolant Technology of Power Reactors, Am. Nuc. Soc., pp. 214-219 (General Background) (undated).
Chemical Engineers' Handbook, Perry, Fifth Edition, McGraw Hill, New York, 1983, pp. 16-1 through 16-50.

*Primary Examiner*—Ernest G. Therkorn

[57] ABSTRACT

This invention relates to a process of and apparatus for the continuous and selective separation of boron-10 ($B^{10}$) isotope having high neutron capture cross-section from boron-11 ($B^{10}$) isotope from a mixture of boron isotopes in a boric acid solution by using a weak base ion exchange resin and water eluant in a continuous annular chromatograph. The invention is a continuous, steady-state, method for separating boron isotopes in aqueous boric acid solutions, including the steps of: (A) preparing an aqueous boric acid feed solution comprising a mixture of boron isotopes; (B) loading the boric acid feed solution onto an ion exchange resin, preferably a weak base anion exchange resin, contained in an ion exchange column of a continuous annular chromatograph at a location on the column, the ion exchange column having a sufficient length and width to resolve isotopes of boron, especially the boron-10 and the boron-11 isotopes into distinct product fractions; (C) feeding an aqueous eluant, preferably water, onto the ion exchange resin in the column of the continuous annular chromatograph at a location on the column to elute the boric acid feed solution along the length of the column of said continuous annular chromatograph and to effect separation of the isotopes in the feed solution.

18 Claims, 4 Drawing Sheets

BORON ISOTOPE SEPARATION USING CONTINUOUS ION EXCHANGE CHROMATOGRAPHY

FIELD OF THE INVENTION

The invention relates to the separation of boron isotopes or the like, by using ion exchange chromatography. Even more particularly, this invention relates to a process of and apparatus for the continuous and selective separation of boron-10 ($B^{10}$) isotope having high neutron capture cross-section from boron-11 ($B^{11}$) isotope from a mixture of boron isotopes by using a weak base ion exchange resin and water eluant in a continuous annular chromatograph.

BACKGROUND OF THE INVENTION

The rate of nuclear fission reactions in a nuclear reactor operations are a function of the number of neutrons available to carry on the neutron triggered chain reaction. Many of the design features of nuclear reactors are based upon their impact on the neutron economy. In particular, materials for use in nuclear reactors are selected for their thermal neutron capture cross-sections, along with other properties. Low neutron capture cross-section materials are selected for reactor components, such as support structures, fuel rod claddings, moderators, etc. High neutron capture cross-section materials are selected for control rods, poison shims, etc. A "poison shim" is a high neutron capture cross-section material added in a carefully selected quantity to decrease neutron flux early in a nuclear fuel cycle, and to become transparent or neutral after neutron absorption such that late in the fuel cycle more of the fission neutrons are absorbed by the fissionable fuel.

In particular, nuclear poisons or shims are typically dissolved in the nuclear coolant fluids, such as in the water coolant loop, for reactor control in nuclear power plants, such as pressurized water reactors (PWRs) nuclear power plants. A poison shim for a nuclear reactor is selected from a chemical compound that meets the following conditions: 1. the solubility and cross-section must be such as to provide the design absorption characteristics in the coolant, and 2. the compound must be chemically and physically stable over the whole range of operating conditions of the nuclear power plant. Boron as boric acid fulfills both of these conditions having a neutron capture cross-section of 755 (0.025 eV) and a maximum required concentration of 0.32 molality, and further possesses the required physical and chemical stability over the full range of operating conditions in PWRs. Boric acid is therefore typically dissolved in the coolant loop, namely the primary water coolant loop, in PWRs. Boric acid ($B(OH)_3$) solutions are added to the PWR nuclear power plant fluid systems at the beginning of the nuclear fuel life cycle when natural fission product poisons are low. As the fission product poisons build up, the boric acid concentration is decreased. This approach allows a given load of nuclear fuel to be kept in the reactor for a longer period of time, thereby reducing maintenance costs.

The boron-10 ($B^{10}$) isotope is particularly useful when dissolved in control fluids in the nuclear power plants. $B^{10}$ isotope has a high thermal neutron capture cross-section and as such is responsible for nuclear reactor control due to its effectiveness in absorbing neutrons. Natural boric acid (NBA) solutions are composed of two stable isotopes of boron, namely high neutron capture cross-section boron-10 ($B^{10}$) and low neutron capture cross-section boron-11 ($B^{11}$) in an atomic ration of $B^{10}:B^{11}$ of about 19.78:80.22. It is known, however, that the $B^{10}$ isotope is responsible for nuclear reaction control due to its neutron capturing ability. The $B^{10}$ isotope has a thermal neutron capture cross-section of about 3836 barns ($10^{-24}$ $cm^2$), and the $B^{11}$ isotope has a thermal neutron capture cross-section of about 5 millibarns. It is desirable to separate the $B^{10}$ from the $B^{11}$ isotopes and provide a $B^{10}$ enriched boric acid (EBA) solution in the nuclear reactor fluid systems to maximize the neutron capturing ability of these solutions, thereby allowing lower boric acid concentrations to be used which accordingly reduces corrosion levels in the primary systems.

However, $B^{10}$ enriched boric acid (EBA) solutions, which contain an atomic ratio of $B^{10}$ to $B^{11}$ atomic ratio in excess of about 19.78:80.22 are not currently employed in reactor fluid systems since the production of $B^{10}$ enriched boric acid solutions are highly expensive and uneconomical. The replacement of natural boric acid (NBA) solutions with $B^{10}$ enriched boric acid (EBA) solutions in PWR nuclear power plants to effect a lower boric acid concentration in all of the reactor fluid systems, would create opportunities to achieve numerous benefits such as reduced radioactive waste volume, improved material performance, higher equipment availability, reduced maintenance, elimination of heat tracing, lower radiation levels, increased plant availability, extended fuel cycles, simplified plant operations, and potential for plant life extension.

A number of methods are known for increasing (enriching) the $B^{10}$ content of boron compounds. These methods include distillation, solvent extraction, and ion exchange of boron compounds. The most significant obstacle, however, preventing the conversion of operating nuclear power plants with $B^{10}$ enriched boric acid solutions is the current high cost for enriching boron. Boron-10 enriched boric acid solutions am not currently employed in the nuclear reactor fluid systems, since the enriched solutions may cost as much as $2.00–$3.00 (U.S.) per gram of 92% $B^{10}$ enriched boric acid solution using presently available $BF_3$ distillation techniques. Whereas the reactor grade natural boric acid solution may only cost $0.001 (U.S.) per gram. It has been shown in cost benefit studies that an acceptable cost of $B^{10}$ enriched solutions can be at most $1.00 (U.S.) per gram of $B^{10}$ enriched solution. It is clearly desirable to enrich boron containing solutions in its $B^{10}$ isotope using an inexpensive process.

Researchers have investigated into the feasibility of boron isotope separation using ion exchange techniques. Kotaka, et al., "Separation of Boron Isotope by Means of Weak Base Anion Exchange Resin", Japan Chemical Society, vol. 8, p. 1482 (1973), teach a batchwise approach for boron isotope separation using ion exchange of aqueous boric acid solutions with weak base anion exchange resins. In this study, aqueous solutions of boric acid were passed through ion exchange columns containing 20–50 mesh anion exchange resin beads, depositing borate ions on the resin. The resin was then eluted with water and the $B^{10}$ isotope content of the effluent fractions were found to be enriched in the $B^{10}$ isotope at the end of the elution. The best separation factor achieved was 1.03 at an operating temperature of 25° C., a boron loading of 50 ml of 0.101M natural boric acid solution, and an elution rate of 38 ml/hr/cm² in a 0.8 cm²×48 cm² test column. It was also shown that higher operating temperatures and higher boron loadings tended to reduce the separation factor. The $B^{10}$ enriched solution was separately collected on the trailing edge of elution.

In other work, Y. Sakuma, et al., "Boron Isotope Separation By Ion Exchange Chromatography Using Weakly Basic Anion Exchange Resin", Bull. Chem. Soc. Jpn., vol. 53, no. 7, pp.1860–1863 (1980), teach another batchwise approach to enrich a natural boric acid solution in the $B^{10}$ isotope from 19.78% to 91% by feeding the feed solution through a 80–100 mesh weakly basic anion exchange resin in a 256 m long ion exchange column using water as the eluant. The natural boric acid feed concentration was 0.1 mole/dm³ and the elution rate was 20 cm³/hr/cm² at an operating temperature of 40° C. The separation factor achieved was constant along the column and was calculated as about 1.0100±0.0005 per 100 cm. The $B^{10}$ enriched fraction was collected on the trailing edge of elution. However, the foregoing batchwise approaches while achieving good separation factors are uneconomical in practice since they require a plurality of batch columns connected in series to achieve the desired separation which is undesirable due in part to the high capital costs and operating maintenance costs.

Attempts have been made to reduce the cost of using enriched boric acid solutions in the fluid systems of nuclear power plants. U.S. Pat. No. 5,176,885 (Impink, Jr., et al.) teaches an in plant method integrated into existing nuclear power plant systems to effect boron-10 isotope enrichment of boric acid solutions by using ion exchange resins capable of the, thermally storing and releasing boron isotopes. Impink, Jr., by using existing boron concentration controllers and heat exchangers, effects boron-10 isotope separation in ion exchangers by repeated cold (about 50° F.) deposition of dilute boric acid solutions on a strong base anion exchange resin and hot (about 140° F.) elution of dilute boric acid solutions on the strong base anion exchange resin, thereby utilizing the property of boric acid to form borate anions with either one or three boron atoms contained within the molecule depending upon the solution temperature. However, after considering the operational problems likely to be encountered by operating a nuclear power plant system while enriching boron, it was decided to evaluate out of plant enrichment schemes.

It would be desirable to provide a low cost and efficient method of and apparatus for $B^{10}$ isotope enrichment of boric acid solutions for use in the fluid systems of nuclear power plants.

SUMMARY OF THE INVENTION

It is an object of the invention to provide a method of and an apparatus for enriching transition element solutions in a desired isotope.

It is another object of the invention to provide a method of and an apparatus for enriching boron solutions in the boron-10 isotope.

It is another object of the invention to provide a relatively low cost method to produce $B^{10}$ isotope enriched boric acid solutions for later use in nuclear reactor control fluids.

It is another object of the invention to provide a method of and an apparatus for separating boron isotopes using ion exchange chromatography which can be performed continuously in a single operation.

It is a feature of the invention to effect $B^{10}$ and $B^{11}$ isotopic separation in boric acid solutions in a continuous annular chromatograph with boric acid solution as the feed phase, water as the eluant or mobile phase, and weak base anion exchange resin as the stationary phase.

It is an advantage of the invention to continuously isolate and collect distinct and separated isotope product fractions always at the same angular position along the length of the ion exchange column.

The invention resides in a continuous method for separating boron isotopes in aqueous boric acid solutions, comprising the steps of: (A) preparing an aqueous boric acid feed solution comprising a mixture of boron isotopes; (B) loading said boric acid feed solution onto an ion exchange resin, preferably a weak base anion exchange resin, contained in an ion exchange column of a continuous annular chromatograph at a location on the column, the ion exchange column having a sufficient length and width to resolve isotopes of boron, especially the boron-10 and the boron-11 isotopes into distinct product fractions; (C) feeding an aqueous eluant, preferably water, onto the ion exchange resin in the column of the continuous annular chromatograph at a location on the column to elute the boric acid feed solution along the length of the column of said continuous annular chromatograph and to effect separation of the isotopes in the feed solution; (D) continuously rotating said continuous annular chromatograph during steps (B) and (C) while said boric acid feed solution and said eluant solution diffuse through said ion exchange resin to effect separation of boron isotopes in the feed solution into distinct product fractions so that each product fraction is angularly and longitudinally displaced from the feed location along the length of the column; (E) separately collecting the distinct boron-10 enriched isotope product fractions and the distinct boron-10 depleted isotope fractions at distinct angularly displaced locations on the continuous annular chromatograph; (F) separately volume reducing the distinct boron isotope product fractions to form concentrated boron isotope fractions and to recover the aqueous eluant therefrom; (G) recycling the aqueous eluant for reuse in step (C). The boron-10 enriched boric acid product fraction, preferably at least 90% boron-10 enriched, can be transported to nuclear power plant facilities to be dissolved in the control fluid systems of the nuclear plants as a poison shim. The boron-10 depleted product fraction can be produced for non-nuclear purposes such as glass making where isotope abundance is not relevant or can be returned to the continuous annular chromatograph for further processing. The eluant can be recycled to maintain low liquid waste concentrations.

The invention also resides in a apparatus for providing an inventory of boron-10 isotope enriched boric acid solutions, comprising: (A) at least one boric acid feed solution source tank; (B) at least one eluant water source tank; (C) at least one continuous annular chromatograph having at least one feed port near the top of said continuous annular chromatograph for carrying the boric acid feed solution from said feed source tank to the continuous annular chromatograph, at least one eluant port near the top of said continuous annular chromatograph for carrying said the eluant solution from said eluant source tank to the continuous annular chromatograph at a position angularly displaced from the boric acid feed port, a rotatable annular ion exchange chromatographic column filled with a weak base anion exchange resin having a sufficient height and diameter to resolve boron isotopes into at least two distinct isotope product fractions, at least one boron-10 enriched product fraction and at least one boron-10 depleted product fraction, at least two product collection ports near the bottom of the annular column positioned at different angular positions which separately collects at least two distinct isotope product fractions; (D) at least one concentrator connected to the product collection ports to separately concentrate and recover the at least two distinct isotope product fractions and to extract the water eluant therefrom into a eluant recycle port; (E) at least one eluant deionizer connected to said eluant recycle port to purify the eluant and connected to the eluant storage tank for reuse in the annular column of the continuous annular chromatograph. The boron-10 isotope enriched boric acid solution has an atomic ratio of boron-10 to boron-11 isotopes in excess of a 19.78% to 80.22% for use in control fluids of nuclear power plants.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

DETAILED DESCRIPTION OF THE PREFERRED EMBODIMENTS

The invention is a method of and apparatus for isotope enrichment of the transition elements (i.e., the elements of the periodic table having a partially filled to filled d electron orbitals (e.g., Zn, Cd, B, etc.)) which are capable of forming water soluble weakly acidic solutions and which are amenable to ion exchange with a weakly basic anion exchange resin. Preferably, the invention is used to enrich a boric acid solution in the boron-10 ($B^{10}$) isotope. The $B^{10}$ enriched boric acid solution has significant commercial value when used in control fluids in nuclear power plants.

The economically feasible isotope enrichment of these transition elements which form water soluble weakly acidic solutions (i.e., incompletely dissociate into ions in aqueous solutions) is accomplished by passing an acidic solution of the element of interest and an eluant solution, respectively, through an ion exchange chromatographic column filled with a basic anion exchange resin which functions in a continuous and steady-state manner to effect continuous separation and isolation of solutions containing isotopes of interest in a single operation, and recycling the eluant solution used to effect separation to consequently generate minimal liquid wastes. It is preferred that boric acid solutions are enriched in the boron-10 isotope according to the method and apparatus of the invention. The invention will hereinafter be described with reference to boron isotope enrichment, but it should be understood that the invention is not limited to boron enrichment.

Natural boric acid (NBA) solutions are composed of two stable isotopes of boron with mass numbers (protons+neutrons) of 10 and 11. As used herein, the term "boron-10" or "$B^{10}$" refers to the boron isotope having a mass number of 10 and the term "boron-11" or "$B^{11}$" refers to the boron isotope having a mass number of 11. A natural boric acid (NBA) solution is defined herein as having an atomic ratio of $B^{10}$ to $B^{11}$ isotopes of about 19.78:80.22. An enriched boric acid (EBA) solution is defined herein as having an atomic ratio of $B^{10}$ to $B^{11}$ isotopes of in excess of about 19.78:80.22.

Figure 1:
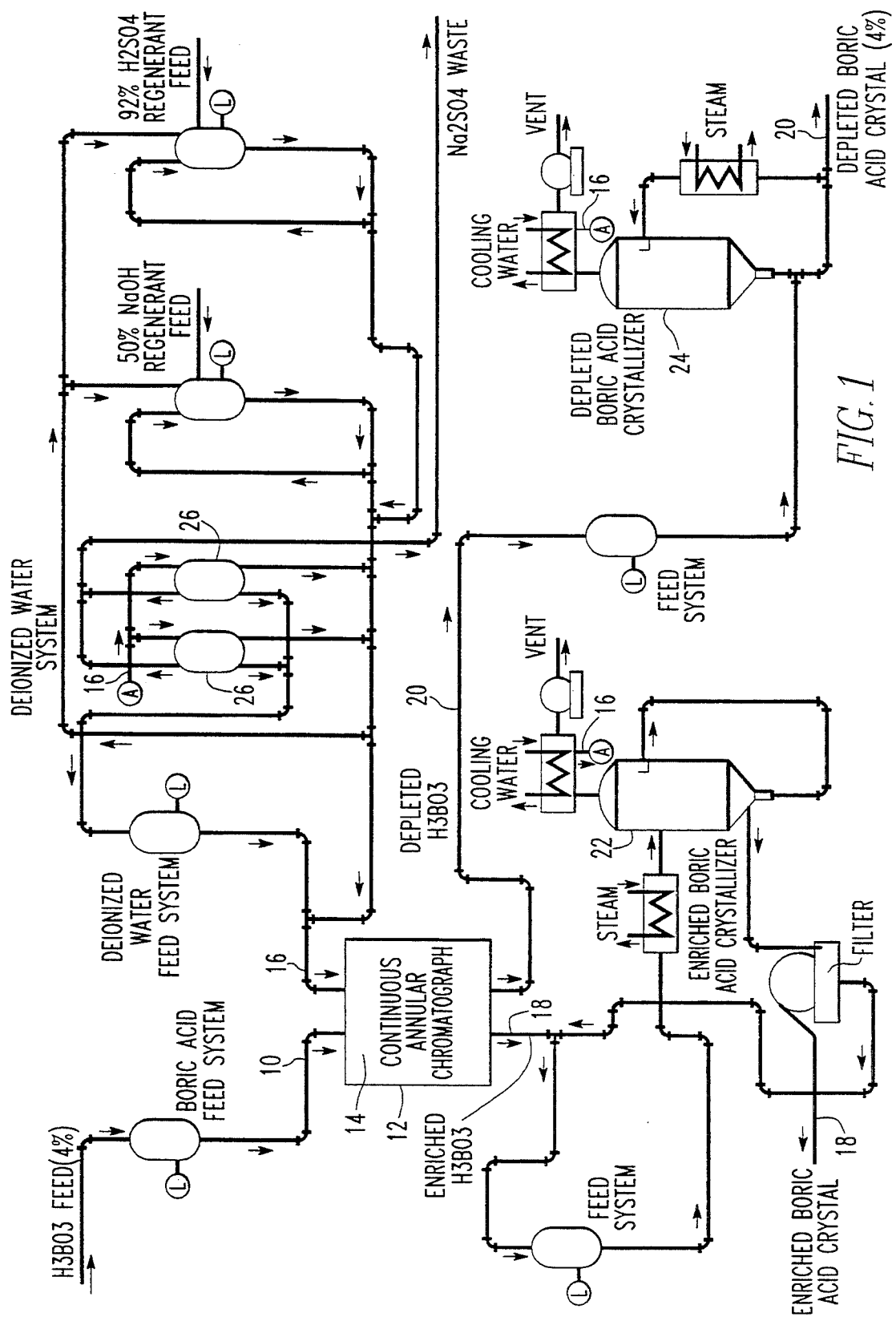
FIG. 1 is a schematic flow diagram showing a representative plant configuration to be used to generate a boron-10 enriched boric acid solution according to the method of and apparatus for the invention.

Referring now to the drawings, FIG. 1 is a schematic illustration of the process and apparatus of the invention for continuous, steady-state, separation of transition element isotopes from a mixture of such isotopes. The preferred starting material for use in the present process is a weakly acidic aqueous mixture of boron isotopes and it is preferred in the process of the invention to enrich the boric acid solution in the boron-10 ($B^{10}$) isotope. In the method of the invention, the starting material or feed phase for the $B^{10}$ isotope enrichment process can be any convenient solution of ionic boron compounds which are weakly acidic in aqueous solution and amenable to ion exchange using a basic, preferably a weakly basic, anion exchange resin. An aqueous boric acid solution, i.e., $B(OH)_3$, is the preferred starting material since it is weakly acidic in aqueous solutions, incompletely ionizing into borate ions, i.e., $B(OH)_4^-$, which is amenable to anion exchange with a basic anion exchange resin. The boron isotope mixture in the boric acid feedstock may be that which occurs in nature (i.e., a NBA solution) or it may be a partially refined mixture obtained from a preliminary enrichment process (i.e., an EBA solution), although a natural boric acid solution is preferred.

The boric acid solution feed stock 10 is fed to an ion exchange chromatographic column 12, preferably a column which functions in a continuous, steady-state manner, even more preferably a continuous annular chromatograph, containing an ion exchange resin or stationary phase 14, whereupon the borate ions containing the $B^{10}$ isotopes of the boric acid solution are preferentially adsorbed onto the stationary ion exchange resin 14. The ion exchange resin can be a weak or strong base anion exchange resin, although a weak base anion exchange resin is preferred. In anion exchange, an $OH^-$ group is liberated from the ion exchange resin, and replaced by the anion in solution, i.e., $B(OH)_4^-$.

Once the borate ions from the feedstock are adsorbed on the anion exchange resin in the column, an eluant solution or mobile phase 16 is fed to the anion exchange resin in the column, whereupon the molecules containing the $B^{10}$ isotopes are preferentially desorbed or stripped from the resin, being solvated in the eluant such that the molecules containing substantially the $B^{10}$ isotopes 18 can be eluted down the column at a differing rate and collected separately from the molecules containing substantially the $B^{11}$ isotopes 20. The eluant solution 16 is a solution capable of solvating borate ions. It is preferred to use water as the eluant since water is effective at solvating the borate ions adsorbed on a weak base ion exchange resin, and further since water minimizes the boric acid recovery efforts. Other eluants, such as strong bases, for example, sodium hydroxide, potassium hydroxide, etc. can be used; however these are not preferred since an additional cost of separating the boric acid from the eluant would add to the cost of the system.

The collected $B^{10}$ enriched boric acid product fraction 18 is directed to a concentrator 22, such as a conventional evaporative crystallizer, and a product of $B^{10}$ enriched boric acid crystals is formed for storage and/or transferred for use in control fluids of nuclear power plants. The collected $B^{10}$ depleted (i.e., $B^{11}$ enriched) boric acid product fraction 20 is directed to a concentrator 24, such as a conventional evaporative crystallizer, and a product of $B^{11}$ enriched boric acid crystals is formed for either return to the continuous ion exchange chromatographic column 12 for further processing or for use in non-nuclear applications, such as glass-making.

The water eluant or other eluant collected from the concentrators, 22 and 24, is treated in a deionizer/ion exchanger 26 such as a conventional mixed bed ion exchanger containing both anion and cation exchange resins wherein the eluant is deionized to maintain a high level of purity and is then recycled to the separation column 12 for reuse. The deionizer, once depleted, is regenerated with acidic and basic solutions, such as sulfuric acid and sodium hydroxide solutions. The continuous annular chromatograph 12, once depleted, can also be regenerated with basic solutions, such as sodium hydroxide solution.

Figure 2:
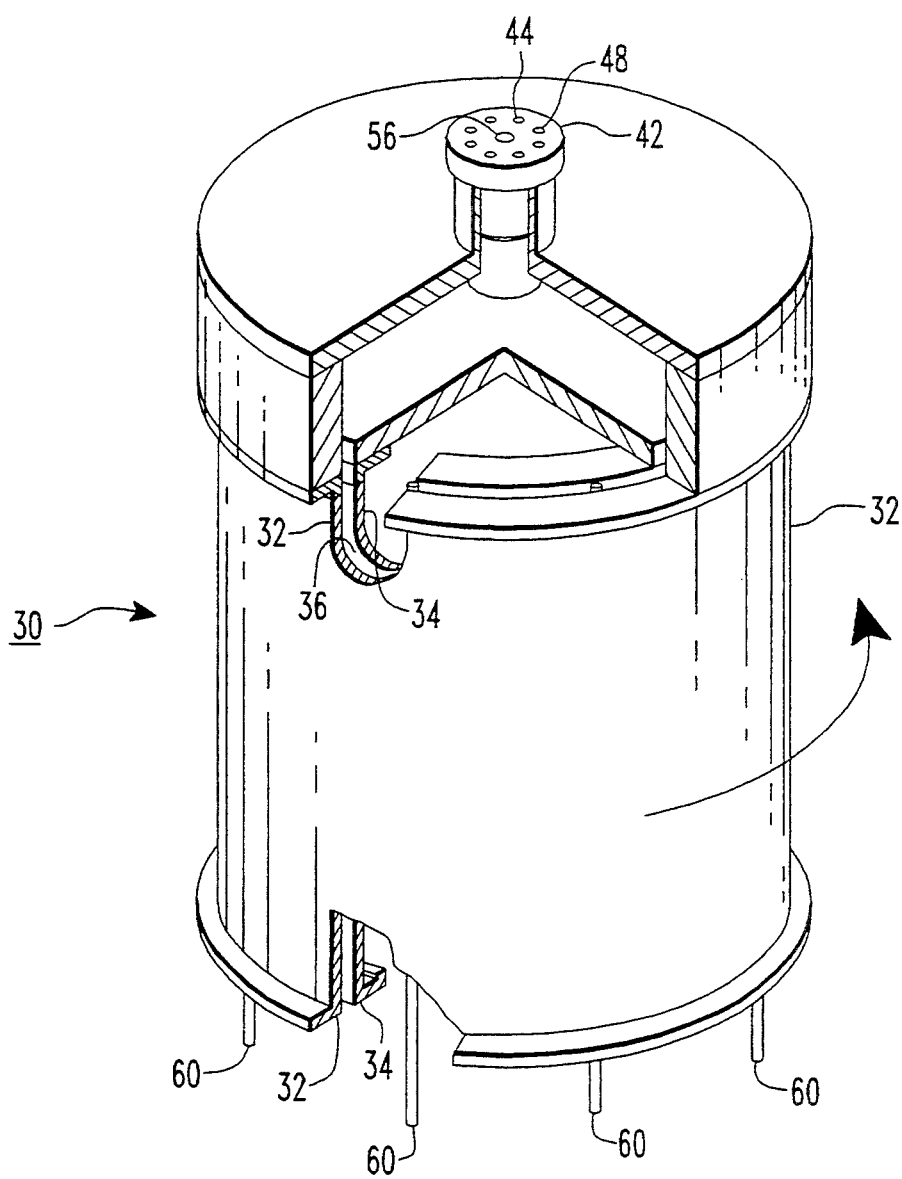
FIG. 2 is a perspective view of an embodiment of a continuous annular chromatograph with a portion in section to illustrate the annular construction suitable for use in the method of and apparatus for the invention.
Figure 3:
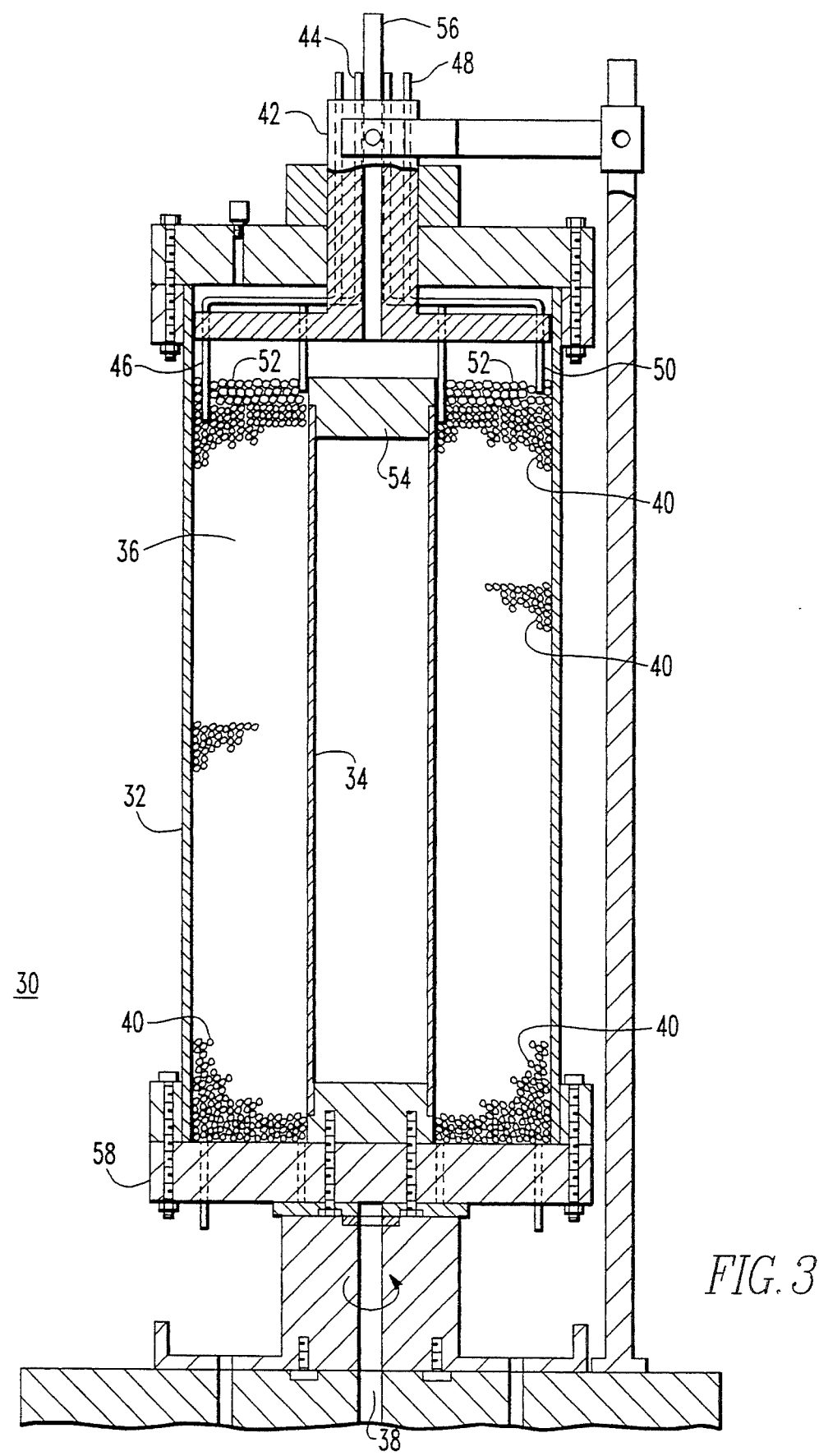
FIG. 3 is a horizontal sectional view of the continuous annular chromatograph of FIG. 2 along a diameter of the concentric circles defining the annulus; and, FIG. 4 is diagrammatic illustration of the separation of boron-10 isotopes from boron-11 isotopes distinctly produced in the continuous annular chromatograph and recoverable at different angular displacements as a function of the elution time along the length of the continuous annular chromatograph.

A continuous, steady-state operating ion exchange chromatograph, such as a continuous annular chromatograph that is preferred for use in the method of the invention has unexpectedly established an economical approach for boron isotope enrichment in a single operation which has not heretofore been taught or suggested in the prior studies which have identified ion exchange techniques as a method of separating boron isotopes. A particularly preferred continuously operating continuous annular chromatograph is shown in FIG. 2 and FIG. 3. Referring now to FIG. 2 and FIG. 3, a continuous annular chromatograph 30 comprises two concentric cylinders 32 and 34 which define an annular space 36 to serve as the ion exchange column. The annular space 36 is rotatable about the axis of the annulus by a shaft 38 and motor (not shown). Ion exchange resins 40 (shown in FIG. 3 as only partially filling the annular space for ease of illustration), preferably weak base anion exchange resin, preferably in the form of spherical beads, are packed between the two concentric cylinders 32 and 34 in the annular space 36 to form an annular ion exchange column. Atop the annular space 36 is a distributor plate 42. Feed pipes 44 and 48 extend through the distributor plate and terminate in feed nozzles 46 and 50, respectively.

The feed pipes 42 and feed nozzles 46 are located at a given angular position atop the packed ion exchange resin annular space 36 and supply a boric acid feed solution to the ion exchange resin beads 40. The feed pipes 48 and feed nozzles 50 are located at an annular offset position from the boric acid solution feed ports and supply an eluant solution, preferably water, to the ion exchange resin beads 40 after the feed solution has been adsorbed thereon to elute boron isotopes therefrom. It is preferred that the boric acid feed solution feed ports extend directly atop the resin beads while the eluant feed ports are somewhat shorter and only extend to a layer of glass beads 52 which sits atop the ion exchange resin beads. This preferred feed arrangement serves to prevent any undesired mixing effects of the feed solution and the eluant. The central cavity defined by the inner cylinder 34 is sealed by a cap 54 so that a pressure pipe 56 can be used to apply pressure to the annular bed of ion exchange resin beads 40.

The continuous annular chromatograph 30 also includes a product plate 58 at the bottom of the annular space 36. A plurality of product delivery channels or collection ports 60 extend though the product plate 58 to the angular space 36 set at different angular positions along the length of the annular space 36 to receive various distinct isotope product fractions which have a set traversed distance down the ion exchange resin beads 40. Each product port 60 collect is positioned to an elution volume which has had a particular residence time in the annular ion exchange column 36. During operation, the continuous, steady-state, annular ion exchange column 36 packed with the ion exchange resin beads 40 is rotated about the axis of the annulus at a constant speed so that arty vertical segment of the annular bed is above a particular fixed collection port 60 at a given time after this segment has been loaded with boric acid solution feed and eluant solution. Thus, each product collection port 60 has an angular position which corresponds to a particular elution time for a particular rate of rotation of the annular space 36 and for a particular flow rate through the resin beads. The flow rate across the effective height of the resin beads and the rotational speed of the resin beads should be coordinated such that a particular product fraction always elutes at the same angular position, and, accordingly is always delivered to the same product collection port.

For boric acid solution separation, at least one product collection port 60 collects the $B^{10}$ enriched boric acid fraction while at least one other product collection port 60 collects the $B^{10}$ depleted boric acid fraction. It is preferred however that a plurality of collection pore 60 be used to collect a particular product fraction. This is accomplished by closely spacing these collection ports so that they span the angular range of rotation that corresponds to the elution time interval of that particular fraction, but they do not extend to the angular positions at which any significant portion of any other product fraction is expected to elute. A more detailed description of the operation of a continuous annular chromatograph and the equations and variables for the design thereof can be found in U.S. Pat. Nos. 5,098,678 (Lee, et al.) and 5,112,493 (Snyder, et al.), both disclosures being incorporated by reference herein.

In a preferred method of the invention, the boric acid solution feed has a concentration of boron as high as is possible without exceeding the solubility limit for the solute in the aqueous solvent under the anticipated operating conditions. The natural consequence of ion exchange chromatographic separation is a dilution via elution of the isotope products being separated into distinct product streams. Therefore, the overall efficiency of the boron isotope enrichment process and particularly the minimization of the efforts needed to recover the desired products is optimized by using as high a concentration of boric acid solution without causing the boric acid to precipitate out during the enrichment process.

The CRC *Handbook of Physics and Chemistry* lists the solubility of boric acid ($B(OH)_3$) in water as 6.35 g/100 cc $H_2O$ at 30° C. and as 27.6 g/100 cc $H_2O$ at 100° C. The preferred concentration of boric acid solution fed to the continuous annular chromatograph operated at ambient temperature is about 0.1 to 1 molar, more preferably 0.5 to 1 molar, and even more preferably near the solubility limit of the feed solution. The temperature of the boric acid solution is preferably in the range of 20° C. to 80° C.; however, it most preferred to operate at ambient temperature of about 20° C. The boric acid solution loading rate to the column is preferably about 0.01 to 1.0 lb/ft$^2$, more preferably about 0.05 to 0.15 lb/ft$^2$.

The eluant is any aqueous solution capable of solvating the boron ions from the ion exchange resin such that they can be eluted down the annular ion exchange column of the continuous annular chromatograph. The eluant can be selected from the group of $H_2O$, NaOH, KOH, CsOH, LiOH, or Phenol and the like. Water is however the preferred eluant in the method of the invention, since the use of water eliminates the need for use of additional complicated separation steps to recover the boric acid solution from the eluant. Elution volumes should be kept as low as is possible to effect substantially complete separation of the boron isotopes in order for the recovered product streams to be highly concentrated. It is preferred to maximize the concentration of the product because the total volume of fluid to be processed will be reduced. This allows a reduction in the overall size of the system and consequently a reduction in costs.

The temperature of the elution is preferably in the range of 20° C. to 80° C.; however, it most preferred to operate at ambient temperature of about 20° C. The eluant flow rate is preferably in the range of 0.01 to 10 gpm/ft$^2$, preferably about 0.1 to 5 gpm/ft$^2$. The eluant flow rate is controlled by the pressure drop across the effective height of the ion exchange resin and the particle size and packing void volume of the resin. The pressure drop required for a given flow rate is preferably provided by pressurizing the continuous annular chromatograph. The pressure drop can be about 1 to 100 psi, more preferably about 5 to 20 psi. It is preferred to operate the continuous annular chromatograph in a displacement mode which may be effected by either an isocratic or gradient supply of eluant.

The ion exchange resin is a weak or strong base anion exchange resin with an affinity for boron ions in aqueous solution. It is preferred to use a weak base anion exchange resin since water can be used as the eluant to strip the borate ions from the resin and elute them down the column to effect separation while also yielding a commercially acceptable separation factor. Weak base anion exchange resins are characterized by active amino groups on a solid matrix such as polystyrene. A more detailed description of the basic anion exchange resins which can be used in the method of the invention are taught in *Perry's Chemical Engineers Handbook*, sixth edition, pp. 16-1 to 16-48 (1984), the disclosure being incorporated by reference herein. An example of a preferred weak base anion exchange resin which can be used in the method of the invention is Amberlite IRA-94 manufactured by Rohm and Haas Chemical Corporation of Philadelphia, Pa. The anion exchange resin is preferably in the form of beads, preferably spherical beads, having an average particle size of about 74 to 840 microns in diameter, preferably about 105 to 250 microns in diameter. The rotational speed of the resin in the continuous annular chromatograph is preferably about 0.001 to 1 ft/min, more preferably about 0.005 to 0.05 ft/min.

It is desired in the method of the invention to produce a $B^{10}$ enriched boric acid solution having an isotope, purity of $B^{10}$ atomic in excess of the natural 19.78% (atomic), preferably of at least 90% (atomic), more preferably at least 92% (atomic). The 92% $B^{10}$ enriched boric acid solution will find its primary application in fluid systems of nuclear power plants, to optimize the neutron absorbing capability of the boric acid solution. The effective continuous annular chromatograph column height should be sufficient to allow significant resolution of the various isotopes of boron, i.e., $B^{10}$ and $B^{11}$ isotopes, into distinct product fractions which can be collected at different angular positions along the column in the collection ports. It is preferred that the desired resolution is affected in a single pass through the continuous annular chromatograph. It is preferred to achieve a separation factor (i.e., used to define the separation capacity of the enrichment process per foot of column height) for the boron-10 isotope enrichment in a continuous annular chromatograph using a weak base ion exchange resin and a water eluant of about 1.01 to 1.20, preferably in excess of 1.10. A preferred column height for 92% $B^{10}$ enrichment process of boric acid solution having a separation factor per foot of 1.11 is about 20 to 40 ft with an outside diameter of about 10 to 20 ft and an annular diameter of 3 to 10 ft.

Figure 4:
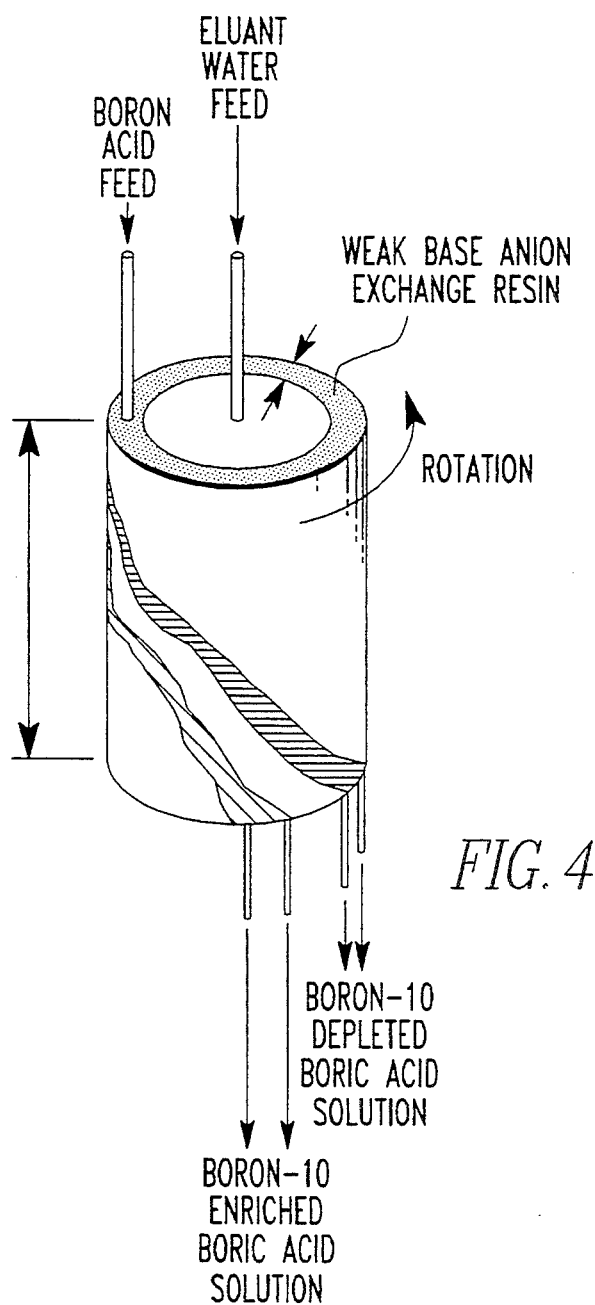

Referring now to FIG. 4, the figure illustrates diagrammatically separation of product fractions in the boric acid feed solution after the feed solution has been eluted with water through a weak base anion exchange resin during rotation of the continuous annular chromatograph. The two product fractions of concern are the $B^{10}$ enriched boric acid solution fraction and the $B^{10}$ depleted boric acid fraction. As the continuous annular chromatograph is continuously rotated, the product fractions in the feed solution are separated so that they are angularly displaced from the feed inlet and collected at collection ports located at the given angular displacement along the length of the column. The product fraction is coordinated to always elute at the same angular position and is thus always collected at the same collection port as shown.

Table 1 below sets forth the preferred continuous annular chromatograph operating conditions for achieving efficient and effective separation of 92% $B^{10}$ isotope from a natural boric acid solution.

TABLE 1

|  | Range | Preferred |
| --- | --- | --- |
| Boric Acid Concentration | 1 to 4 w/o | 4 w/o |
| Boric Acid Solvent | Water, Bases | Water |
| Boric Acid Loading | 0.01 to 1 lb/ft$^2$ | ~0.01 lb/ft$^2$ |
| Ion Exchange Resin | Weak or Strong Base Anion Exchange Resin | Weak Base Anion Exchange Resin |
| Particle Size | 74 to 840 microns | ~149 microns |
| Particle Shape | Spherical or Irregular | Spherical |
| Eluant | Strong or Weak Bases, Water | Water |
| Elution Flow Rate | 0.01 to 10 gpm/ft$^2$ | ~1 gpm/ft$^2$ |
| Column Height | 20 to 40 ft | ~30 ft |
| Outer Column Diameter | 10 to 20 ft | ~12 ft |
| Inner Column Diameter | 3 to 10 ft | ~5 ft |
| Separation Factor | 1.01 to 1.20 | ~1.10 |

TABLE 1-continued

| | Range | Preferred |
|---|---|---|
| Rotational Speed | 0.001 to 1 ft/min | ~0.02 ft/min |

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

We claim:

1. A continuous, steady-state, ion exchange chromatographic method for concurrently separating transition element isotopes from a mixture of these isotopes in order to produce substantially pure fractions of each of the transition element isotopes, comprising the steps of:
   (a) subjecting a feed solution of transition element ions to continuous, steady-state ion exchange chromatography with an ion exchange resin and an eluant, wherein said transition element is boron, said feed solution is natural boric acid solution, said ion exchange resin is weak base anion exchange resin, and said eluant is water;
   (b) concurrently collecting a separate isotope for each of the isotopes present in the feed solution.

2. The method of claim 1, wherein said continuous, steady-state ion exchange chromatography is effected in a continuous annular chromatograph.

3. A continuous method for separating transition element isotopes selected from the group consisting of boron, cadmium, and zinc in weakly acidic aqueous solution, comprising the steps of:
   (a) preparing a weakly acidic aqueous feed solution of a transition element selected from the group consisting of boron, cadmium, and zinc comprising a mixture of transition element isotopes;
   (b) loading said feed solution onto an ion exchange resin contained in an annular column of a continuous annular chromatograph;
   (c) feeding an aqueous eluant onto said ion exchange resin to elute said feed solution along said annular column of said continuous annular chromatograph;
   (d) continuously rotating said continuous annular chromatograph during steps (b) and (c) while said feed solution and said eluant solution diffuse through said ion exchange resin;
   (e) separately collecting distinct transition element isotope product fractions at distinct locations on the continuous annular chromatograph;
   (f) separately volume reducing said distinct isotope product fractions to form concentrated isotope fractions and recovering said aqueous eluant therefrom;
   (g) recycling said aqueous eluant for reuse in step (c).

4. The method of claim 3, further comprising the step of:
   (h) continuously repeating steps (a) to (g) to produce commercially useful quantities of isotopically separated fractions.

5. The method of claim 3, wherein said ion exchange resin is selected from the group consisting of strong base anion exchange resins and weak base anion exchange resins.

6. The method of claim 3, wherein said aqueous eluant is selected form the group consisting of water, NaOH, KOH, CsOH, LiOH, and phenol.

7. The method of claim 3, wherein said ion exchange resin is a weak base anion exchange resin and said aqueous eluant is water.

8. A continuous method for separating boron isotopes in aqueous boric acid solutions, comprising the steps of:
   (a) preparing an aqueous boric acid feed solution comprising a mixture of boron isotopes;
   (b) loading said boric acid feed solution onto an ion exchange resin contained in an annular column of a continuous annular chromatograph at a first location at the top of said annular column having a vertical height and diameter sufficient to resolve isotopes of boron into distinct product fractions;
   (c) feeding an aqueous eluant onto said ion exchange resin of said continuous annular chromatograph at a second location angularly displaced from the first location at the top of said annular column to elute said boric acid feed solution along said annular column of said continuous annular chromatograph;
   (d) continuously rotating said continuous annular chromatograph during steps (b) and (c) while said boric acid feed solution and said eluant solution diffuse through said ion exchange resin to effect separation of boron isotopes in the feed solution into distinct product fractions so that each product fraction is angularly and longitudinally displaced from the first location along the length of the annular column;
   (e) separately collecting said distinct boron isotope product fractions at distinct angularly displaced locations on the continuous annular chromatograph;
   (f) separately volume reducing said distinct boron isotope product fractions to form concentrated boron isotope fractions and recovering said aqueous eluant therefrom;
   (g) recycling said aqueous eluant for reuse in step (c).

9. The method of claim 8, further comprising the step of:
   (h) continuously repeating steps (a) to (g) to produce commercially useful quantities of isotopically separated fractions.

10. The method of claim 8, wherein said ion exchange resin is selected from the group consisting of strong base anion exchange resins and weak base anion exchange resins.

11. The method of claim 12, wherein said ion exchange resin is selected from the group consisting of weak base anion exchange resins.

12. The method of claim 8, wherein said aqueous eluant is selected form the group consisting of water, NaOH, KOH, CsOH, LiOH, and phenol.

13. The method of claim 12, wherein said aqueous eluant is water.

14. The method of claim 8, wherein said method operates at ambient temperature.

15. The method of claim 8, wherein said boric acid feed solution concentration is about 0.1 to 1.0M.

16. The method of claim 8, wherein said ion exchange resin are spherical resin beads having an average particle size of about 74 to 840 microns in diameter.

17. The method of claim 8, wherein steps (e), (f) and (g) comprises the steps of:
   (i) separately collecting at least one boron-10 isotope enriched boric acid solution product fraction and at least one boron-10 depleted boric acid solution product fraction;

(ii) separately volume reducing each of said at least one boron-10 enriched and at least boron-10 depleted boric acid solution product fractions by evaporating said aqueous eluant therefrom to form concentrated boron-10 enriched and boron-10 depleted boric acid crystals;

(iii) recovering the aqueous eluant from step (ii) and deionizing the aqueous eluant for reuse in step (c).

18. The method of claim 8, wherein the boric acid feed solution is a natural boric acid solution.

* * * * *